(12) United States Patent
Seymour et al.

(10) Patent No.: US 12,048,450 B2
(45) Date of Patent: Jul. 30, 2024

(54) DEVELOPABLE AND COLLAPSABLE INTERNAL CUTTING MECHANISM

(71) Applicant: Brigham Young University, Provo, UT (US)

(72) Inventors: Kendall H. Seymour, Springville, UT (US); Jacob Sheffield, Provo, UT (US); Lance Hyatt, Provo, UT (US); Scott Cunnington, Provo, UT (US); Spencer P. Magleby, Provo, UT (US); Larry L. Howell, Orem, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 18/204,554

(22) Filed: Jun. 1, 2023

(65) Prior Publication Data

US 2023/0320746 A1 Oct. 12, 2023

Related U.S. Application Data

(63) Continuation of application No. 17/277,010, filed as application No. PCT/US2019/051712 on Sep. 18, 2019, now abandoned.

(Continued)

(51) Int. Cl.
*A61B 17/32* (2006.01)
*A61B 17/22* (2006.01)
*A61B 17/3207* (2006.01)

(52) U.S. Cl.
CPC .. *A61B 17/32002* (2013.01); *A61B 17/22031* (2013.01); *A61B 17/320016* (2013.01);
(Continued)

(58) Field of Classification Search
CPC .... A61B 2017/32004; A61B 17/32002; A61B 2017/320032; A61B 17/22031;
(Continued)

(56) References Cited

U.S. PATENT DOCUMENTS 3,630,105 A * 12/1971 Rider ................... H02G 1/1265
 81/9.51
4,327,609 A  5/1982 Resch
(Continued)

FOREIGN PATENT DOCUMENTS

JP  2006095312 A  4/2006
JP  2016028652 A  3/2016
(Continued)

OTHER PUBLICATIONS

International Search Report for International Application No. PCT/US2019/051712 mailed Dec. 3, 2019.
(Continued)

*Primary Examiner* — Shaun L David
*Assistant Examiner* — Mitchell Brian Hoag
(74) *Attorney, Agent, or Firm* — Dorsey & Whitney LLP

(57) ABSTRACT

A hollow rod developable actuator tool including a first link comprising an outer cylinder, a second link comprising a first tool member pivotably connected to the first link at a first joint mounted in a first cavity in the wall of the outer cylinder, a third link comprising a second tool member pivotably connected to the first tool member at a second link, and a fourth link comprising an inner cylinder to which the second tool member is also pivotably connected at a third link mounted in a second cavity in the wall of the inner cylinder. When the inner cylinder of the fourth link is rotated in relation to the outer cylinder of the first link the actuator tool transitions from a first state where the tool is closed to a second state where the tool is open.

15 Claims, 4 Drawing Sheets

Related U.S. Application Data

(60) Provisional application No. 62/732,892, filed on Sep. 18, 2018.

(52) U.S. Cl.
CPC ............. *A61B 2017/320024* (2013.01); *A61B 2017/320028* (2013.01); *A61B 2017/320032* (2013.01); *A61B 2017/32004* (2013.01); *A61B 2017/320078* (2017.08); *A61B 2017/320082* (2017.08); *A61B 17/320783* (2013.01)

(58) Field of Classification Search
CPC ............ A61B 17/320783; A61B 17/32; A61B 17/2804; A61B 17/2909; A61B 17/295; A61B 2017/2845; A61B 2017/2901; A61B 2017/2903; A61B 2017/2908; A61B 2017/2912; A61B 2017/2919; A61B 2017/2933; A61B 2018/00202; A61B 2090/034; A61B 2017/00353; A61B 17/142; A61B 17/16; A61B 2017/320024; A61B 2017/320028; A61B 17/320036; A61B 2017/320075; A61B 2017/320077; A61B 2017/320078; A61B 2017/32008; A61B 2017/320084; A61B 17/32053; A61B 17/320016; A61B 2017/320775; A61B 2017/320791; A61B 17/3209; A61B 17/32093; A61B 2017/32096; A61B 17/3211; A61B 2017/32113; A24F 13/24; A61F 13/26
USPC ........................................................ 606/170
See application file for complete search history.

(56) References Cited

U.S. PATENT DOCUMENTS

| | | | |
|---|---|---|---|
| 5,010,797 A | 4/1991 | Stepan | |
| 5,509,923 A | 4/1996 | Middleman et al. | |
| 6,215,081 B1 | 4/2001 | Jensen et al. | |
| 8,382,423 B1 * | 2/2013 | Frodis | A61B 17/3201 |
| | | | 415/904 |
| 10,492,822 B2 * | 12/2019 | Chen | A61B 17/3203 |
| 2005/0251167 A1 | 11/2005 | Voegele et al. | |
| 2007/0250096 A1 * | 10/2007 | Yamane | A61B 17/22 |
| | | | 606/159 |
| 2008/0234725 A1 | 9/2008 | Griffiths et al. | |
| 2009/0018565 A1 | 1/2009 | To et al. | |
| 2010/0173563 A1 | 7/2010 | Su | |
| 2012/0191121 A1 * | 7/2012 | Chen | A61B 17/3203 |
| | | | 606/180 |
| 2013/0084180 A1 | 4/2013 | Conley et al. | |
| 2014/0114138 A1 | 4/2014 | Fedorov et al. | |
| 2014/0276920 A1 * | 9/2014 | Hendrick | A61B 18/245 |
| | | | 606/127 |
| 2016/0051127 A1 | 2/2016 | Yoshimura | |
| 2016/0051274 A1 | 2/2016 | Howell et al. | |
| 2017/0196588 A1 * | 7/2017 | Schuman | A61B 17/320758 |
| 2017/0354470 A1 | 12/2017 | Farritor et al. | |
| 2018/0078276 A1 * | 3/2018 | Chen | A61B 10/0266 |
| 2018/0177516 A1 | 6/2018 | Vardi et al. | |
| 2021/0100581 A1 * | 4/2021 | Gilliland | A61B 17/3423 |
| 2022/0032442 A1 * | 2/2022 | Sheffield | B25J 19/023 |

FOREIGN PATENT DOCUMENTS

| | | |
|---|---|---|
| WO | 2020061181 A1 | 3/2020 |
| WO | 2020061190 A1 | 3/2020 |
| WO | 2020112217 A1 | 6/2020 |

OTHER PUBLICATIONS

International Search Report for International Application No. PCT/US2019/051727 mailed Dec. 6, 2019.

International Search Report for International Application No. PCT/US2019/051728 mailed May 5, 2020.

Notice of Allowance for U.S. Appl. No. 17/277,010 mailed Mar. 3, 2023.

Supplemental Notice of Allowability for U.S. Appl. No. 17/277,010 mailed Mar. 20, 2023.

Nelson, et al., "Developable Mechanisms on Developable Surfaces", Brigham Young University disclosure 2018-032, Jun. 14, 2018, 29 pages.

* cited by examiner

DEVELOPABLE AND COLLAPSABLE INTERNAL CUTTING MECHANISM

CROSS-REFERENCE TO RELATED APPLICATIONS

This application is a continuation of U.S. patent application Ser. No. 17/277,010 filed Mar. 17, 2021, which is a U.S. Nationalization of PCT International Application No. PCT/US2019/051712 filed Sep. 18, 2019, which claims priority to, and the benefit of, U.S. Provisional Application 62/732,892, filed Sep. 18, 2018, for all subject matter common to both applications. The disclosure of said provisional application is hereby incorporated by reference in its entirety.

STATEMENT REGARDING FEDERALLY SPONSORED RESEARCH OR DEVELOPMENT

This invention was made with government support under NSF Award No. 1663345 awarded by the National Science Foundation. The government has certain rights in the invention.

FIELD OF THE INVENTION

The present invention relates to tools, and more specifically to actuating mechanisms disposed within hollow rods suitable for performing tasks such as cutting, gripping, and/or squeezing, objects inside the hollow rod.

BACKGROUND

Generally, in the field of tools having actuating mechanisms disposed within hollow cylindrical shafts, tubes, or rods, conventional tools often allow only one mechanism to operate at the end of the rod. This is especially the case when the inner cross-sectional areas of the hollow rods are small. For example, down-hole drilling equipment, minimally invasive surgical tools, and the like, often make use of a single tool to operate at the distant/distal end of the shaft/tube/rod and are representative of such shaft, tube, or rod type tool implementations.

SUMMARY

There is a need for hollow rod developable actuator tools having multiple developable actuating mechanisms disposed within hollow rods having small cross-sectional areas. The present invention is directed toward further solutions to address this need, in addition to having other desirable characteristics.

In accordance with embodiments of the present invention, a hollow rod developable actuator tool is provided. The hollow rod actuator includes a first link comprising an outer cylinder, a second link comprising a first tool member, a third link comprising a second tool member, and a fourth link comprising an inner cylinder.

The outer cylinder of the first link includes a first end having an first aperture, a second end having a second aperture, a first wall extending between the first end and second end defining an outer circumference of the hollow rod and a central passage therethrough from the first end to the second end, and a first cavity disposed in the first wall having a first joint mounted therein.

The first tool member of the second link includes a first end pivotably coupled to the first wall of the first link at the first joint, a second end, a body extending between first end and second end having a contact area, and a second joint offset from the first joint on the body of the second link;

The second tool member of the third link includes a first end pivotably coupled to a third joint, a second end pivotably coupled to the body of the second link at the second joint, and a body extending between the first end and second end having a contact area;

The inner cylinder of the fourth link is disposed within the central passage of the outer cylinder of the first link and includes a first end having a first aperture; a second aperture at a second end, a second wall extending between the first aperture and the second aperture defining an inner circumference of the hollow rod and a central passage therethrough from the first end to the second end, and a second cavity in the second wall having the third joint mounted therein and pivotably coupled to the body of the third link.

When the inner cylinder of the fourth link is rotated in relation to the outer cylinder of the first link in such a way that moves the first joint and third joint away from each other along the perimeter of the hollow rod, the actuator tool transitions from a first state wherein the body of the second link and the body of the third link are within the first cavity and the second cavity of the respective first wall and second wall to a second state where the body of the second link is pivoted around the first joint and the body of the third link is pivoted around the third joint extended into the central passage to engage an object in the central passage between the contact areas of the bodies of the second link and third link.

In accordance with aspects of the present invention, when the inner cylinder of the fourth link is rotated in relation to the outer cylinder of the first link in such a way that moves the first joint and third joint toward each other along the perimeter of the hollow rod, the actuator tool transitions from the second state to the first state.

In accordance with aspects of the present invention, at least one of the contact area of the second link and the contact area of the third link is a blade.

In accordance with aspects of the present invention, at least one of the contact area of the second link and the contact area of the third link is a wiper.

In accordance with aspects of the present invention, at least one of the body of the second link and the body of the third link is curved to match a curvature of the first and fourth link making the second link and third link flush with the inner circumference when the actuator tool is in the first state.

In accordance with aspects of the present invention, the first cavity and the second cavity are located in proximity to the first end of the first link and the first end of the fourth link.

In accordance with embodiments of the present invention, a method of using a hollow rod developable actuator tool is provided. The method includes the steps of providing a hollow rod developable actuator tool including a first link comprising an outer cylinder, a second link comprising a first tool member, a third link comprising a second tool member, and a fourth link comprising an inner cylinder; and actuating the hollow rod developable actuator tool.

The first tool member of the second link includes a first end pivotably coupled to the first wall of the first link at the first joint, a second end, a body extending between first end and second end having a contact area, and a second joint offset from the first joint on the body of the second link.

The second tool member of the third link includes a first end pivotably coupled to a third joint, a second end pivotably coupled to the body of the second link at the second joint, and a body extending between the first end and second end having a contact area.

The inner cylinder of the fourth link is disposed within the central passage of the outer cylinder of the first link and includes a first end having a first aperture; a second end having a second aperture, a second wall extending between the first aperture and the second aperture defining an inner circumference of the hollow rod and a central passage therethrough from the first end to the second end, and a second cavity in the second wall having the third joint mounted therein and pivotably coupled to the body of the third link.

When the inner cylinder of the fourth link is rotated in relation to the outer cylinder of the first link in such a way that moves the first joint and third joint away from each other along the perimeter of the hollow rod, the actuator tool transitions from a first state wherein the body of the second link and the body of the third link are within the first cavity and the second cavity of the respective first wall and second wall to a second state where the body of the second link is pivoted around the first joint and the body of the third link is pivoted around the third joint extended into the central passage to engage an object in the central passage between the contact areas of the bodies of the second link and third link.

The hollow rod developable actuator tool is actuated by rotating the inner cylinder of the fourth link in relation to the outer cylinder of the first link in such a way that moves the first joint and third joint away from each other along the perimeter of the hollow rod to transition the second link and third link from a first state to a second state.

In accordance with aspects of the present invention, engaging the object comprises grasping the object between the contact areas of the bodies of the second link and the third link. In other aspects, engaging the object comprises cutting the object between the contact areas of the bodies of the second link and the third link.

In accordance with aspects of the present invention, the method of using the hollow rod developable actuator tool further comprising inserting one or more objects into the central passage. In certain aspects, at least one of the objects is a tool. In some such aspects, the tool can be used to insert other objects into the central passage.

In accordance with aspects of the present invention, the method further comprises rotating the inner cylinder of the fourth link in relation to the outer cylinder of the first link in such a way that moves the first joint and third joint toward each other along the perimeter of the hollow rod to transition the second link and third link from a second state to a first state.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
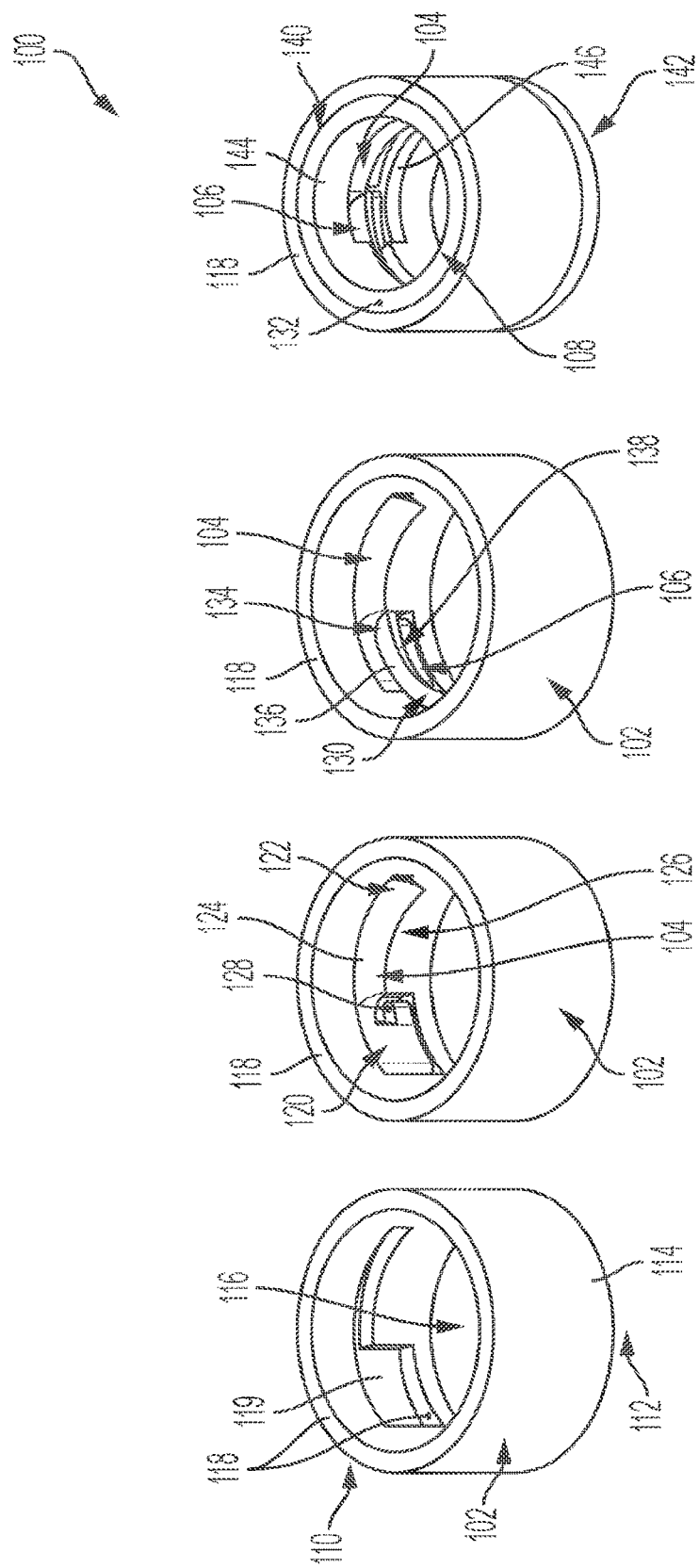
FIG. 1 shows successive images of the various parts of a hollow rod developable actuator tool being assembled together to create an operational tool.

An illustrative embodiment of the present invention relates to a hollow rod developable actuator tool. The tool comprises a cylindrical tube that conceals two curved-link (developable) four-bar mechanisms that can actuate to perform functions such as to cut, grip, squeeze, objects on the inside of the cylinder. When the mechanism is closed, the tube resembles a simple cylindrical tube with constant inner and outer diameter with the mechanism nested inside the tube walls and therefore creates the option of inserting a separate tool, such as a surgical tool, through the tube and past the mechanism. One way to actuate the mechanism is by rotating the inner cylinder with respect to the outer cylinder (see FIG. 2).

A single hollow rod developable actuator tool may enter a workspace through a confined entrance, while a separate tool can be inserted into the workspace through a central passage in the inner diameter of the hollow rod developable actuator tool to perform functions proximal to the end of the cylindrical tube. When desired, the separate tool can be partially retracted to give room for the invention mechanism to perform tasks such as to cut, grip, or squeeze any object inside the interior volume or chamber of the tube. For example, a minimally invasive separate surgical tool may enter a body cavity through the single hollow rod containing the invention mechanism, grip a piece of tissue, retract it partially into the tube or rod, and then actuate the mechanism to cut off a biopsy sample of the tissue. The internal mechanism can be positioned at the end of the tube, with half of the cylinder wall cut away at the end, to allow the scissors or grippers to reach an object without inserting additional tools into the hollow rod.

In other embodiments, a lens or camera may be disposed in the interior volume or chamber of the tube, and the inventive mechanism is configured wipe or otherwise clear the lens or camera when actuated.

FIGS. 1 through 4, wherein like parts are designated by like reference numerals throughout, illustrate an example embodiment or embodiments of a hollow rod developable actuator tool and its use, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

As utilized herein, the term "developable" has a specific meaning. A developable surface is a shape that can be made from a thin sheet of material without breaking or stretching. The term "developable mechanism" or "developable actuator" are interchangeable terms as utilized herein and describe a mechanism that conforms to or is created from a developable surface. Developable mechanisms can conform to or emerge from developable surfaces such as aircraft fuselages and wings, submarine hulls, rocket cones, and minimally invasive surgery tools.

Also as utilized herein, the inventive mechanism contained within the cylindrical tube or rod is considered "closed" when in an un-deployed first state, also referred to as a conformed position, nested inside cavities in the tube walls, and the inventive mechanism is considered "open" when in a deployed second state, expanding outward from the cavities and beyond the tube walls into the central passage.

Figure 2:
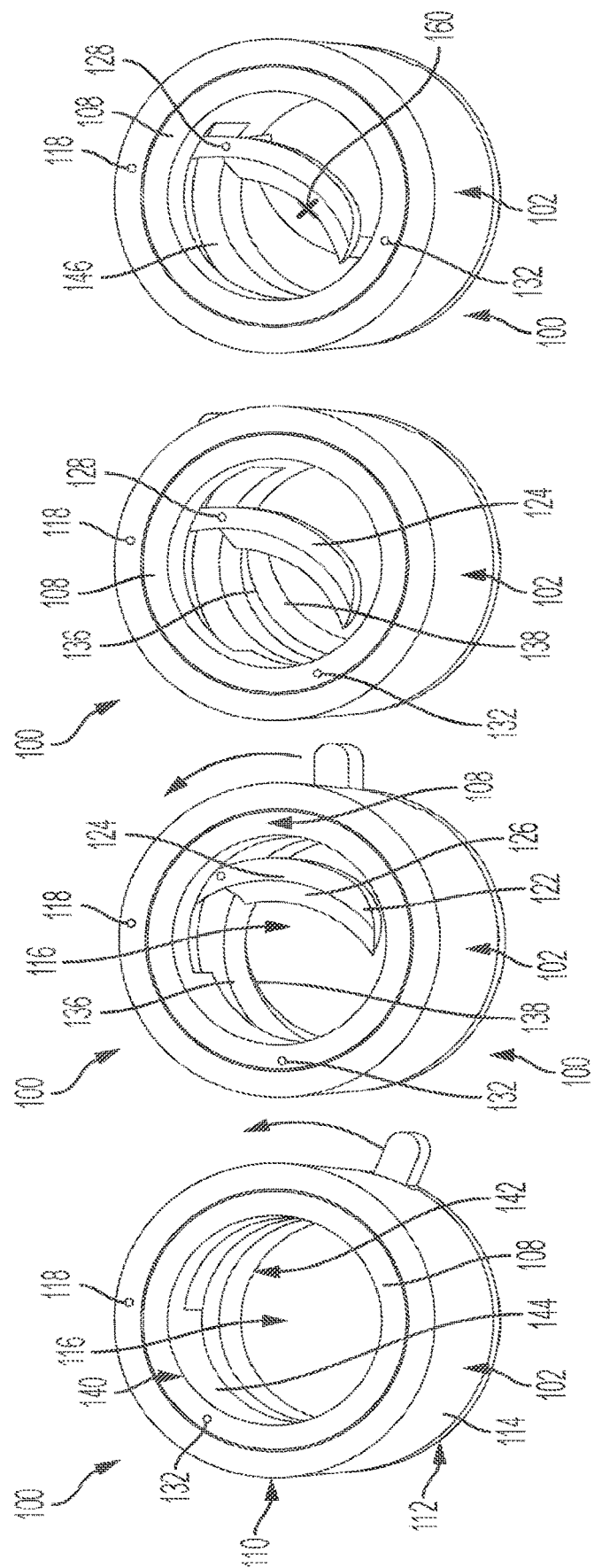
FIG. 2 shows successive images of a hollow rod developable actuator tool with a central cutting and/or gripping developable actuator mechanism as created in FIG. 1, the tool transitioning through different stages of actuation.
Figure 3:
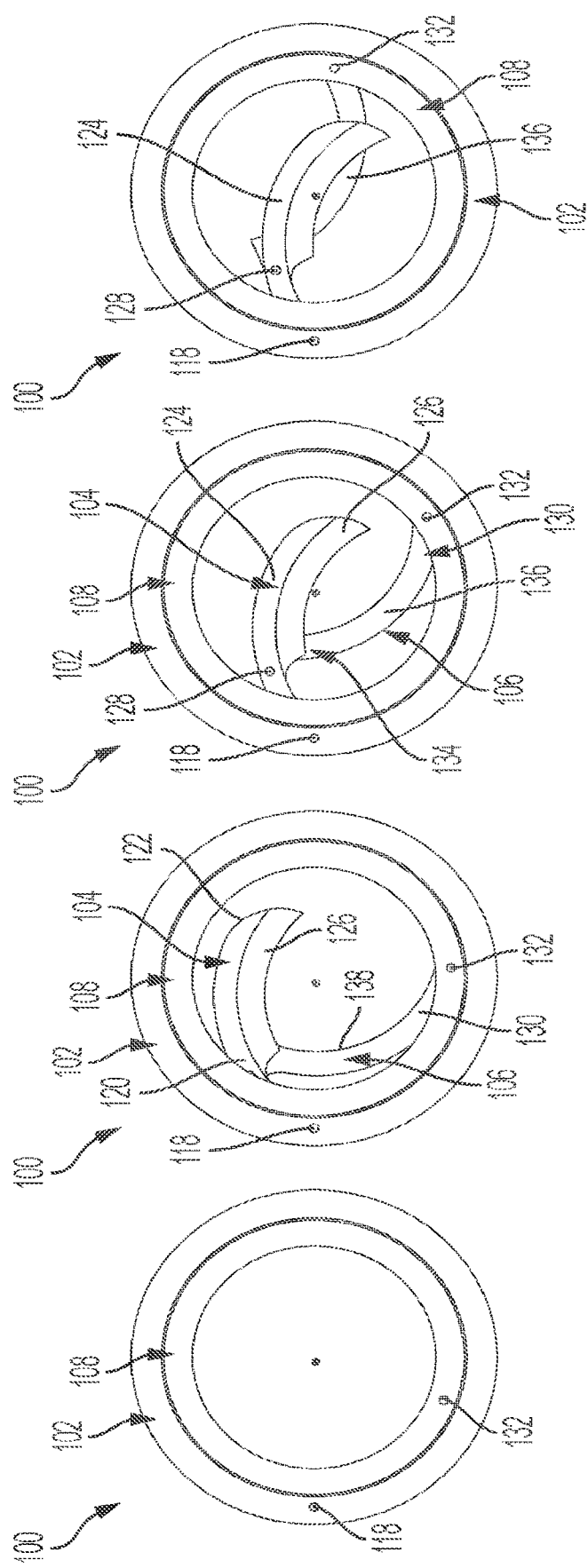
FIG. 3 is a diagrammatic illustration of the hollow rod developable actuator tool of FIG. 2.

FIG. 1 shows successive images of the various elements of the hollow rod developable actuator tool 100 being assembled together. FIG. 2 shows successive images of an assembled hollow rod developable actuator tool 100 in in operation. FIG. 3 shows a 3D computer rendering of the operation of the hollow rod developable actuator tool 100 from a top down perspective in successive images. The hollow rod developable actuator tool 100 as seen in FIG. 1 through FIG. 3 includes two concentric cylinders. A four-bar mechanism, a curved or adapted crank-slider, is fit to the diameter and thickness of the outer cylinder, so that the individual links of the mechanism have the same curvature as the outer cylinder (although this is not a requirement for operation). The elements that make up the four-bar mechanism includes a first link 102 comprising the outer cylinder, a second link 104 comprising a first tool member, a third link 106 comprising a second tool member, and a fourth link 108 comprising the inner cylinder disposed within the central passage 116 of the outer cylinder of the first link 102.

The outer cylinder of the first link 102 (Link 1) can be seen in the first left-most image of FIG. 1. The outer cylinder of the first link 102 has a first end 110 having a first aperture, a second end 112 having a second aperture at, and a first wall 114 extending between the first end 110 and second end 112 defining an outer circumference of the hollow rod developable actuator tool 100 and a central passage 116 therethrough from the first end 110 to the second end 112. A first cavity 119 is disposed in the first wall 114 having a first joint 118 mounted therein.

The first wall 114 of the first link 102 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The outer circumference of the first link 102 as well as the length of the first wall 114 between the first end 110 and the second end 112 may vary depending on the intended use or application of the hollow rod developable actuator tool 100.

The first cavity 119 in the first wall 114 comprises an indent, recess, cut-away, channel, passage, window, or the like that is sized and dimensioned to allow the first tool member of the second link 104 reside or otherwise be stowed in the first cavity 119 when the mechanism of the present device is in a closed position. In the embodiment of FIGS. 1-3 the first joint 118 is a pin and socket assembly embedded in the first wall 114 and spanning the first cavity 119. Other suitable joint devices or mechanism will be apparent to one skilled in the art given the benefit of this disclosure.

The second left-most image of FIG. 1 shows the first tool member of the second link 104 (Link 2) added to the outer cylinder of the first link 102 in the assembly of the tool 100. The first tool member of the second link 104 has a first end 120 pivotably coupled to the first wall 114 of the first link 102 at the first joint 118, a second end 122, a body 124 extending between first end 120 and second end 122 having a contact area 126, and a second joint 128 offset from the first joint 118 on the body 124 of the second link 104. The body 124 of the second link 104 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 124 of the first link 102 is curved to conform to the curvature of the first link 102 such that the body 124 of the second link 104 can reside within the first cavity 119 of the first wall 114 when the mechanism is in a closed state.

The contact area 126 is configured to engage objects within the central passage 116. In certain embodiments, the contact area 126 is a gripping surface. In certain embodiments, such as seen in FIGS. 2 and 3, the contact area 126 is a blade. In still other embodiments the contact area may be a wiper. In certain embodiments, the contact area 126 is formed as part of the body 124 from the same material as the body 124. In other embodiments, the contact area 126 can be formed of a material different from the body and attached to the body 124. In certain embodiments, the contact area 126 is curved to match the curvature of the fourth link 108 such that the contact area 128 is flush with the inner circumference of the fourth link 108 when the mechanism is in a closed state. Other suitable materials and implementations will be apparent to one skilled in the art given the benefit of this disclosure.

The third left-most image of FIG. 1 shows the second tool member of the third link 106 (Link 3) added to the outer cylinder of the first link 102 and first tool member of the second link 104 in the assembly of the tool 100. The second tool member of the third link 106 has a first end 130 pivotably coupled to a third joint 132, a second end 134 pivotably coupled to the body 124 of the second link 104 at the second joint 128, and a body 136 extending between first end 130 and second end 134 having a contact area 138. The body 136 of the third link 106 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 1136 of the third link 106 is curved to conform to the curvature of the fourth link 108 such that the body 124 of the second link 104 can reside within a second cavity 146 in the fourth link 108 and be flush with the inner circumference of the fourth link 108 when the mechanism is in a closed state.

The contact area 138 is configured work in conjunction with the contact area 126 of the second link 104 to engage objects within the central passage 116. In certain embodiments, the contact area 138 is a gripping surface. In other embodiments, such as seen in FIGS. 1 and 2, the contact area 138 is a blade. In still other embodiments, the contact area is a wiper. In certain embodiments, the contact area 138 is formed as part of the body 136 from the same material as the body 136. In other embodiments, the contact area 138 can be formed of a material different from the body and attached to the body 134. Other suitable materials and implementations will be apparent to one skilled in the art given the benefit of this disclosure.

In the embodiment of FIGS. 1-3 the second joint 128 is a pin and socket assembly formed in the body 124 of the second link 104 and the body 136 of third link 106. Other suitable joint devices or mechanism will be apparent to one skilled in the art given the benefit of this disclosure.

The fourth and right-most image of FIG. 1 shows the inner cylinder of the fourth link 108 (Link 4) added to the outer cylinder of the first link 102, first tool member of the second link 104, and second tool member of the third link 106 completing the assembly of the tool 100. The inner cylinder of the fourth link 108 has a first end 140 having a first aperture, a second end 142 having a second aperture, and a second wall 144 extending between the first end 140 and the second end142 defining an inner circumference of the hollow rod and the central passage 116 therethrough from the first end140 to the second end 142. A second cavity 146 is disposed in the second wall 144 having the third joint 132 mounted therein and pivotably coupled to the first end 130 of the body 136 of the third link 106.

The second wall 144 of the fourth link 108 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The inner circumference of the fourth link 108 as well as the length of the second wall 144 between the first end 140 and the second end 142 may vary depending on the intended use or application of the hollow rod developable actuator tool 100.

The second cavity 146 in the second wall 144 comprises a cut-away, channel, passage, window, or the like that is sized and dimensioned to allow the first tool member of the second link 104 pass through the second wall 144 and the second tool member of the third link 106 to reside or otherwise be stowed in the second cavity 146 when the mechanism of the present device is in a closed position. In the embodiment of FIGS. 1-3 the third joint 132 is a pin and socket assembly embedded in the second wall 144 and spanning the second cavity 146. Other suitable joint devices or mechanism will be apparent to one skilled in the art given the benefit of this disclosure. Once assembled, the tool 100 can be actuated to deploy the first and second tool members within the central passage 116. Examples of this operation can be seen in FIG. 2 and FIG. 3 with FIG. 2 providing a perspective view and FIG. 3 providing a top down view.

The depth (or distance along the length of the cylinder) on the first link 102 of the second link 104, third link 106, and fourth link 108 does not change the function of the mechanism. In certain embodiments, the fourth link 108 extends the full length of the first link 102. In certain embodiments, the first cavity of the first wall 114 and the second cavity 146 of the second wall 144 are located in proximity to the first end 110 of the first link 102 and the first end 140 of the fourth link 108. Thus, the second link 104 and third link 106 are also located proximity to the first ends 110, 140. Typically, the first ends 110, 140 would be inserted into the workspace, while the second ends 112, 142 would be proximate to a user. Objects could be inserted into the central passage 116 of the tool at either end of the tool and engaged by mechanism of the tool 100.

Figure 4:
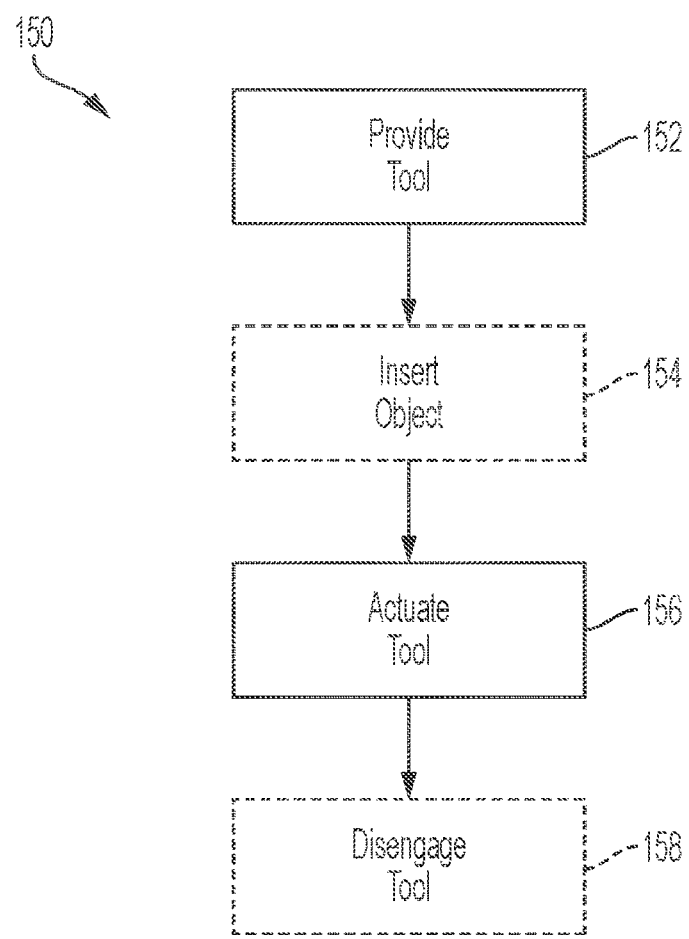
FIG. 4 is a flow diagram depicting a method of using the hollow rod developable actuator tool of the present invention.

FIG. 4 depicts a methodology 150 for using the hollow rod developable actuator tool 100 of the present invention. First a hollow rod developable actuator tool 100 as described herein is provided (Step 152). This tool 100 can be deployed in the particular workspace where hollow rod actuator tools are typically used such as drill site or surgical environment. The tool 100 can then be actuated in the workspace (Step 156) to transition from a first closed state to a second open state wherein the mechanism can be used to interact with an item in the central passage 116 of the tool 100. In certain embodiments, the method 150 further includes additional steps. For example, in certain embodiments one or more objects can be inserted into the central passage of the tool 100 (step 154). The tool 100 may also be transitioned from the second open state back to the first closed state to disengage the tool 100 (Step 158) wherein the tool 100 can be withdrawn from the workspace.

Typically, the second end of the tool 100 would be proximate to a user while the distant first end of the tool 100 would be inserted into the workspace. Objects can be inserted into the central passage 116 of the tool at either end of the tool 100 and engaged by mechanism of the tool 100 (step 154). For example, in some embodiments, one or more tools can be inserted by the user into the central passage 116 through the second end 142 of the fourth link 108 and the second end 112 of the first link 102. Likewise, objects can be inserted into central passage at the distant first end through the first end 140 of the fourth link 108 which resides within the first end 110 of the first link 102. In some such instances, a tool inserted at the second end can used to insert or pull an object into the central passage 116 through the distant first end.

The actuating of the tool 100 (Step 154) is shown in the successive images of FIG. 2 and FIG. 3 moving left to right with the left-most image being the tool 100 in a first closed state and the right most image being the tool 100 in an open second state wherein the tool 100 engages an object in the central passage 116 of the tool 100.

When the inner cylinder of the fourth link 108 is rotated in relation to the outer cylinder of the first link 102 in such a way that moves the first joint 118 and third joint 132 away from each other along the perimeter of the tool 100, as indicated by arrow 148, the actuator tool transitions from a first closed state to a second open state. In the first state, the body 124 of the second link 104 and the body 136 of the third link 106 are within the first cavity (not shown) of the first wall and the second cavity 146 of the second wall 14. In the second state, where the body 124 of the second link 104 is pivoted around the first joint 118 and the body 136 of the third link 106 is pivoted around the third joint 132 and extend into the central passage 116. As the body of 124 of the second link 104 and the body 136 of the third link 106 move toward each other, an object in the central passage 116 is engaged by the contact area 126 of the second link 104 and the contact area 138 of the third link 106.

In some embodiments, the engagement of an object by the contact area 126 of the second link 104 and the contact area 138 of the third link 106 involves grasping the object between the contact area 126 of the second link 104 and the contact area 138 of the third link 106. In other embodiments, such as when at least one of the contact areas 126, 138 are a blade, the engagement of an object by the contact area 126 of the second link 104 and the contact area 138 of the third link 106 involves cutting the object between the contact area 126 of the second link 104 and the contact area 138 of the third link 106. In other embodiments, the contact areas 126, 138 are wipers configured to wipe the surfaces of a lens or camera disposed in the central passage 116.

In certain embodiments, the body 124 of the second link 104 pivots around the first joint 118 and the body 136 of the third link 106 pivots around the third joint 132 in a plane perpendicular to the central passage 116. In certain embodiments, the body 124 of the second link 104 pivots around the first joint 118 in a first perpendicular plane and the body 136 of the third link 106 pivots around the third joint 132 in a second perpendicular plane offset from the first plane. In such embodiments, the second cavity 146 is sized to accommodate the both the body 124 of the second link 104 and the body 136 of the third link 106. In some such embodiments, one or more of the contact areas 126, 138 are a blade the movement of the second link 104 and third link 106 toward each other operates as a scissor to cut an object at the contact point 160 where the contact area 126 of the second link 104 and the contact area 138 of the third link 106 meet and overlap. In other such embodiments, the contact area 126 of the first link 102 may extend into the second plane while the contact area 138 of the third link 106 may extend into the first plane so as to create a co-planar gripping surface between the contact areas 126, 138. Other implementations and configurations will be apparent to one skilled in the art.

In a similar manner, to disengage the tool 100 (Step 156), the inner cylinder of the fourth link 108 is rotated in relation to the outer cylinder of the first link 102 in such a way that moves the first joint 118 and third joint 132 toward each other along the perimeter of the tool 100. This transitions the tool 100 from the second open state to the first closed state.

It is notable that the shape of the links is arbitrary for mechanism motion. As long as the distance between the pins, joints, or axes of rotation between adjacent links remains the same and the links do not self-interfere, the mechanism has the same motion. To completely conceal the moving links when the mechanism is closed, the links are constrained to a similar radius of curvature of the actuating cylinders and/or to a shape that will fit inside the cylinders when fully collapsed.

Conventional cylindrical shaft or tube tools often allow only one tool to operate at the end of the shaft, especially when the tubes are small. The present invention enables an instrument or mechanism to be included in the cylindrical tube and to enter a workspace through a single entrance in combination with other instruments on the end of the shaft. This can i) lower the time required to perform a task in a confined/remote workspace by reducing the number of tooling changes required; ii) reduce the trauma/damage to the boundary of the workspace by reducing the number of entrance holes/points required; iii) reduce trauma/damage to the workspace by limiting interface between the blades/grippers and body tissue, since the only tissue interacting with the blades/grippers is that which is drawn into the inner diameter of the cylindrical shaft; iv) reduce the complexity of the control system used in conjunction with the tooling setup, as fewer shafts would be required to enter the space, and v) reduce the cost of the procedure.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

The invention claimed is:

1. A hollow rod developable actuator tool comprising:
 a first link comprising an outer cylinder, the outer cylinder comprising:
  a first end having a first aperture;
  a second end having a second aperture,
  a first wall extending between the first end and second end defining an outer circumference of the outer cylinder and a central passage therethrough from the first end to the second end;
  a first cavity disposed in the first wall having a first joint mounted therein;
 a second link comprising a first tool member, the first tool member comprising:
  a first end pivotably coupled to the first wall of the first link at the first joint;
  a second end;
  a body extending between first end and second end having a contact area;
  a second joint offset from the first joint on the body of the second link;
 a third link comprising a second tool member, the second tool member comprising:
  a first end pivotably coupled to a third joint
  a second end pivotably coupled to the body of the second link at the second joint;

a body extending between the first end and second end having a contact area;
a fourth link comprising an inner cylinder disposed within the central passage of the outer cylinder of the first link, the inner cylinder comprising:
  a first end having a first aperture;
  a second end having a second aperture;
  a second wall extending between the first end and the second end defining an inner circumference of the inner cylinder and a central passage therethrough from the first end to the second end;
  a second cavity in the second wall having the third joint mounted therein and pivotably coupled to the body of the third link;
wherein, when the inner cylinder of the fourth link is rotated in relation to the outer cylinder of the first link in such a way that moves the first joint and third joint away from each other along the perimeter of the actuator tool, the actuator tool transitions from a first state wherein the body of the second link and the body of the third link are within the first cavity and the second cavity of the respective first wall and second wall to a second state where the body of the second link is pivoted around the first joint and the body of the third link is pivoted around the third joint extended into the central passage to engage an object in the central passage between the contact areas of the bodies of the second link and third link.

2. The hollow rod developable actuator tool of claim 1, wherein when the inner cylinder of the fourth link is rotated in relation to the outer cylinder of the first link in such a way that moves the first joint and third joint toward each other along the perimeter of the actuator tool transitions from the second state to the first state.

3. The hollow rod developable actuator tool of claim 1, wherein at least one of the contact area of the second link and the contact area of the third link is a blade.

4. The hollow rod developable actuator tool of claim 1, wherein at least one of the contact area of the second link and the contact area of the third link is a wiper.

5. The hollow rod developable actuator tool of claim 1, wherein at least one of the body of the second link and the body of the third link are curved to match a curvature of the first and fourth link making the second link and third link flush with the inner circumference when the actuator tool is in the first state.

6. The hollow rod developable actuator tool of claim 1, wherein the first cavity and the second cavity are located in proximity to the second aperture of the first link and the second aperture of the fourth link.

7. The hollow rod developable actuator tool of claim 1, wherein the body of the second link pivots around the first joint in a first plane perpendicular to the central passage and the third link pivots around the third joint in a second plane perpendicular to the central passage and offset from the first plane.

8. A method of using a hollow rod developable actuator tool, the method comprising:
  providing a hollow rod developable actuator tool, the hollow rod developable actuator tool comprising:
    a first link comprising an outer cylinder, the outer cylinder comprising:
      a first end having a first aperture;
      a second end having a second aperture,
      a first wall extending between the first end and second end defining an outer circumference of the outer cylinder and a central passage therethrough from the first end to the second end;
      a first cavity disposed in the first wall having a first joint mounted therein-;
    a second link comprising a first tool member, the first tool member comprising:
      a first end pivotably coupled to the first wall of the first link at the first joint;
      a second end;
      a body extending between first end and second end having a contact area;
      a second joint pivotably coupled with the second link offset from the first joint on the body of the second link;
    a third link comprising a second tool member, the second tool member comprising:
      a first end pivotably coupled to a third joint
      a second end pivotably coupled to the body of the second link at the second joint;
      a body extending between the first end and second end having a contact area;
    a fourth link comprising an inner cylinder disposed within the central passage of the outer cylinder of the first link, the inner cylinder comprising:
      a first end having a first aperture;
      a second end having a second aperture;
      a second wall extending between the first end and the second end defining an inner circumference of the inner cylinder and a central passage therethrough from the first end to the second end;
      a second cavity in the second wall having the third joint mounted therein and pivotably coupled to the body of the third link;
    wherein, when the inner cylinder of the fourth link is rotated in relation to the outer cylinder of the first link in such a way that moves the first joint and third joint away from each other along the perimeter of the actuator tool, the actuator tool transitions from a first state wherein the body of the second link and the body of the third link are within the first cavity and the second cavity of the respective first wall and second wall to a second state where the body of the second link is pivoted around the first joint and the body of the third link is pivoted around the third joint extended into the central passage to engage an object in the central passage between the contact areas of the bodies of the second link and third link;
  actuating the actuator tool by rotating the inner cylinder of the fourth link in relation to the outer cylinder of the first link in such a way that moves the first joint and third joint away from each other along the perimeter of the outer cylinder to transition the second link and third link from a first state to a second state.

9. The method of claim 8, wherein engaging the object comprises grasping the object between the contact areas of the bodies of the second link and the third link.

10. The method of claim 8, wherein engaging the object comprises cutting the object between the contact areas of the bodies of the second link and the third link.

11. The method of claim 8, wherein engaging the object comprises wiping the object with the contact areas of the bodies of the second link and the third link.

12. The method of claim 8, further comprising inserting one or more objects into the central passage.

13. The method of claim 12, wherein at least one of the one or more objects comprises a tool.

14. The method of claim 13, further comprising using the tool to inert another object into the central passage.

15. The method of claim 8, further comprising:
rotating the inner cylinder of the fourth link in relation to the outer cylinder of the first link in such a way that moves the first joint and third joint toward each other along the perimeter of the outer cylinder to transition the second link and third link from a second state to a first state.

* * * * *